US00PP32747P2

(12) United States Plant Patent
Eveleens et al.

(10) Patent No.: US PP32,747 P2
(45) Date of Patent: Jan. 12, 2021

(54) ***HYDRANGEA* PLANT NAMED 'HOKOMALEGA'**

(50) Latin Name: *Hydrangea macrophylla*
Varietal Denomination: Hokomalega

(71) Applicants: Horteve Breeding BV, Aalsmeer (NL); Kolster Holding BV, Boskoop (NL)

(72) Inventors: Cornelis Pieter Eveleens, Aalsmeer (NL); Peter Rudolf Kolster, Boskoop (NL)

(73) Assignees: HORTEVE BREEDING BY, Aalsmeer (NL), part interest; KOLSTER HOLDING BY, Boskoop (NL), part interest ( * ) Notice: Subject to any disclaimer, the term of this patent is extended or adjusted under 35 U.S.C. 154(b) by 0 days.

(21) Appl. No.: 16/602,055

(22) Filed: Jul. 25, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

*Primary Examiner* — Anne Marie Grunberg
(74) *Attorney, Agent, or Firm* — Penny J. Aguirre

(57) ABSTRACT

A new cultivar of *Hydrangea macrophylla* plant named 'Hokomalega' that is characterized by its very floriferous blooming habit, its sterile flowers that have sepals with crenate margins, its inflorescences that are pink in color with a touch of green, and its suitability as a potted plant.

3 Drawing Sheets

Botanical classification: *Hydrangea macrophylla.*
Varietal denomination: 'Hokomalega'.

CROSS REFERENCE TO A RELATED APPLICATION

This application is related to U.S. Plant Patents for a plant derived from the same breeding program that is entitled *Hydrangea* Plant Named 'Hokomac' (U.S. Plant Pat. No. 22,259).

BACKGROUND OF THE INVENTION

The present invention relates to a new and distinct cultivar of *Hydrangea macrophylla* and will be referred to hereafter by its cultivar name, 'Hokomalega'. 'Hokomalega' represents a new bigleaf *Hydrangea*, a perennial shrub grown for landscape use and as a potted plant.

'Hokomalega' derived from an ongoing controlled breeding program directed by the Inventors. An objective of the breeding program included developing a new cultivar of *Hydrangea* with pink flowers, a floriferous blooming habit and other desirable traits.

'Hokomalega' arose from a controlled cross made by the Inventors in Boskoop, The Netherlands in May of 2007 between *Hydrangea* 'Hokomac' as the female parent and *Hydrangea* 'Glowing Alps' (not patented) as the male parent. 'Hokomalega' was selected as a single unique plant from amongst the resulting seedlings in June of 2009.

Asexual propagation of the new cultivar was first accomplished by stem cuttings by one of the Inventors in August of 2009 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomalega' as a unique cultivar of *Hydrangea macrophylla.*

1. 'Hokomalega' exhibits a very floriferous blooming habit.
2. 'Hokomalega' exhibits sterile flowers that have sepals with crenate margins.
3. 'Hokomalega' exhibits inflorescences that are pink in color with a touch of green.
4. 'Hokomalega' exhibits suitability as a potted plant.

The female parent of 'Hokomalega' differs from 'Hokomalega' in having sterile sepals that have more green coloration, less crenate margins and a more flattened mophead. The male parent of 'Hokomalega' differs from 'Hokomalega' in having a darker pink inflorescence and sepals with smooth margins and no green coloration. 'Hokomalega' can be most closely compared to the *Hydrangea macrophylla* cultivars 'Hortmacaro' (U.S. Plant Pat. No. 31,263) and 'Hokomapiclo' (not patented). 'Hortmacaro' and 'Hokomapiclo' are both similar to 'Hokomalega' in having sterile flowers that are pink in color with sepals that have crenate margins. 'Hortmacaro' differs from 'Hokomalega' in having a different shaped mophead, leaves and sterile sepal margins that are more crenate and a firmer sterile sepal texture. 'Hokomapiclo' differs from 'Hokomalega' in having inflorescences that are lighter pink in color, sterile flowers with sepals that are more green in color with larger crenated margins.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new *Hydrangea*. The photographs were taken of a two-year-old plant of 'Hokomalega' as grown in a greenhouse in a 17-cm container in Boskoop, The Netherlands.

The photograph in FIG. 1 provides a side view of the plant habit of 'Hokomalega' in bloom.

Figure 1:
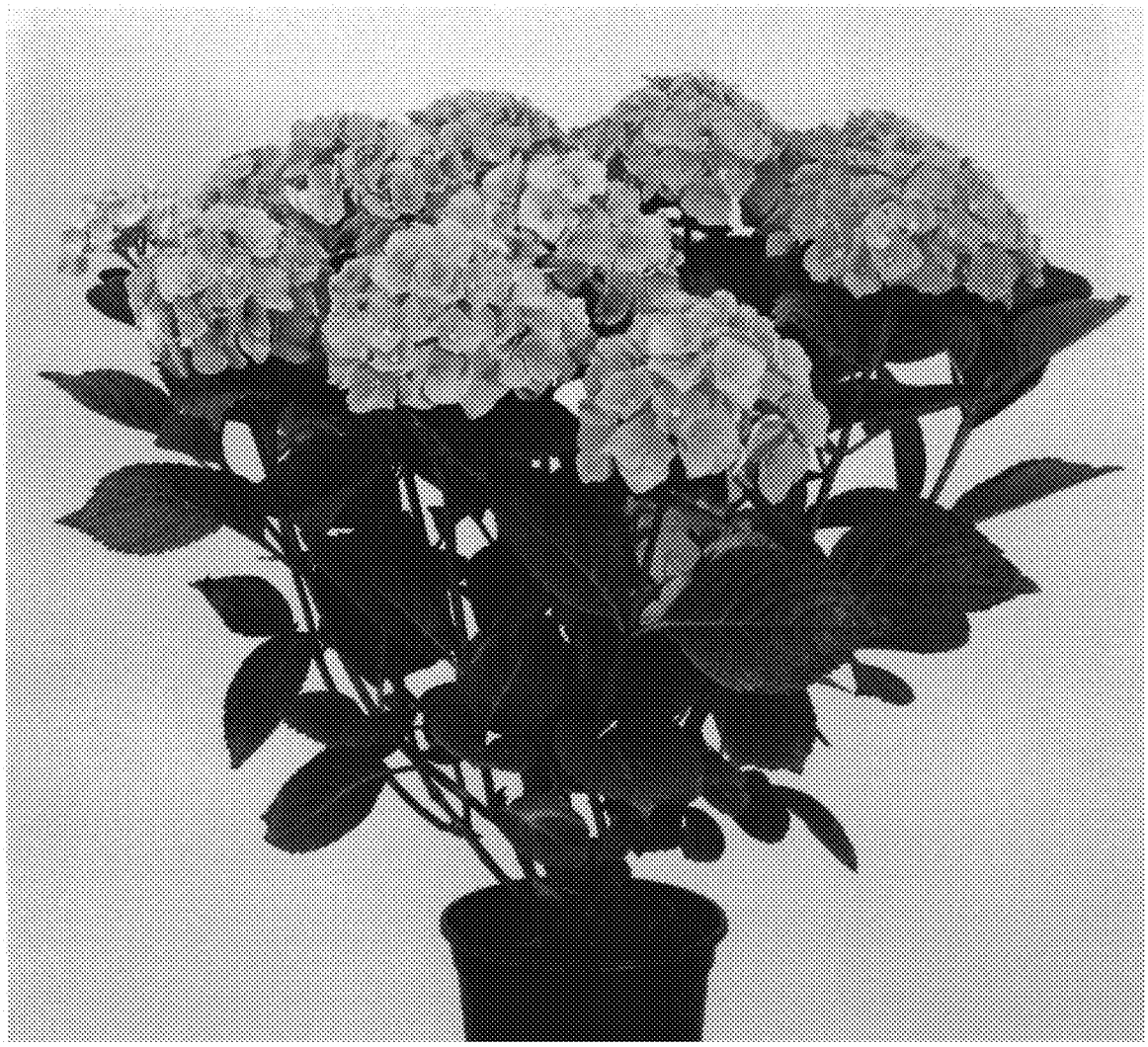
Figure 2:
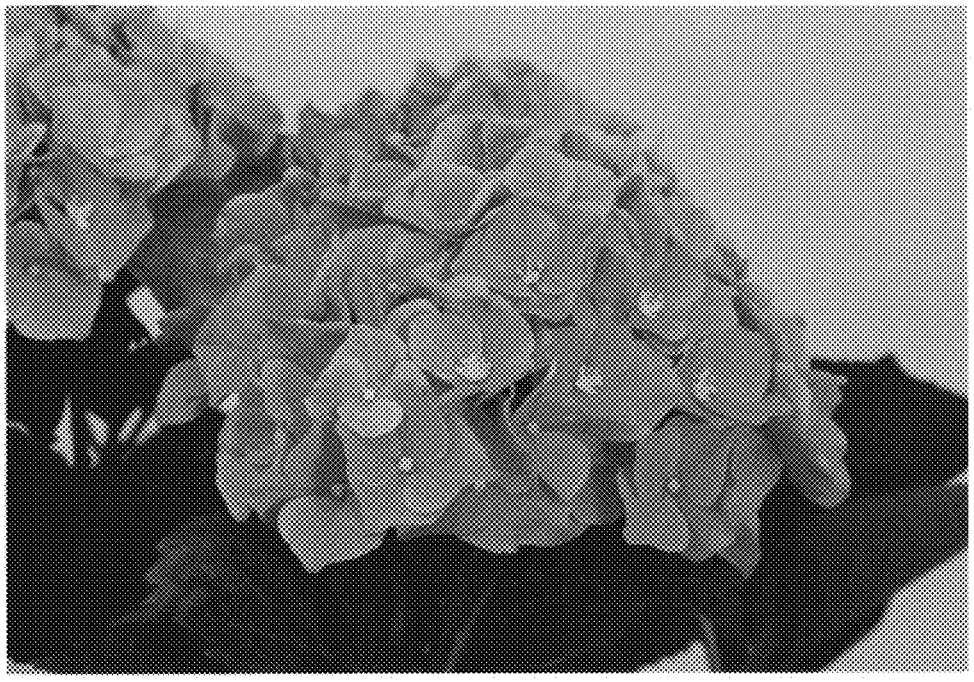

The photograph in FIG. 2 provides a close-up view of a fully open inflorescence of 'Hokomalega'.

Figure 3:
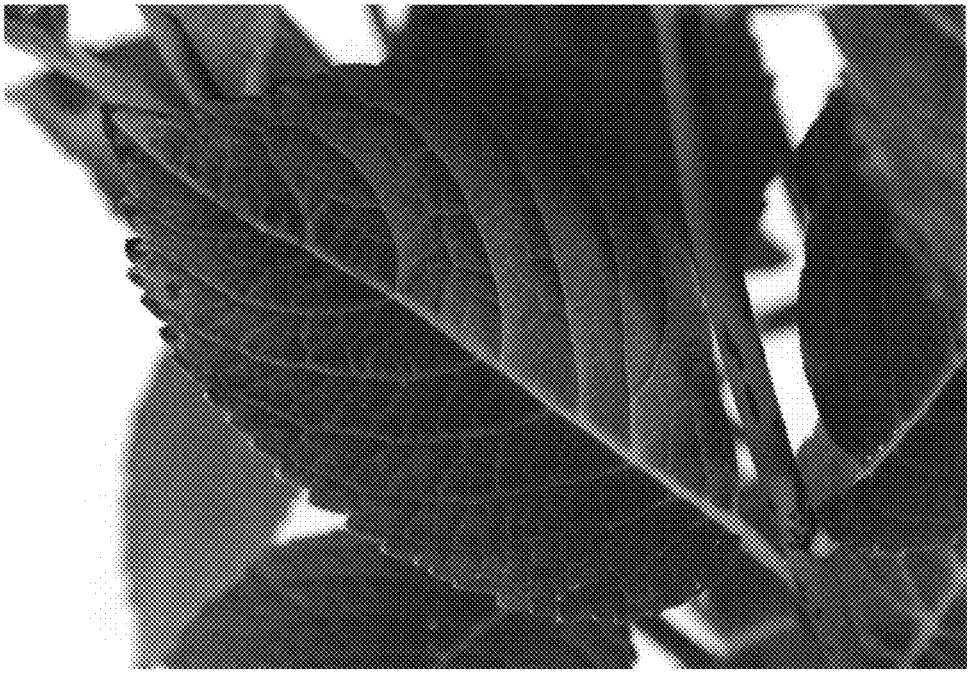

The photograph in FIG. 3 provides a close-up view of the foliage of 'Hokomalega'.

Figure 4:
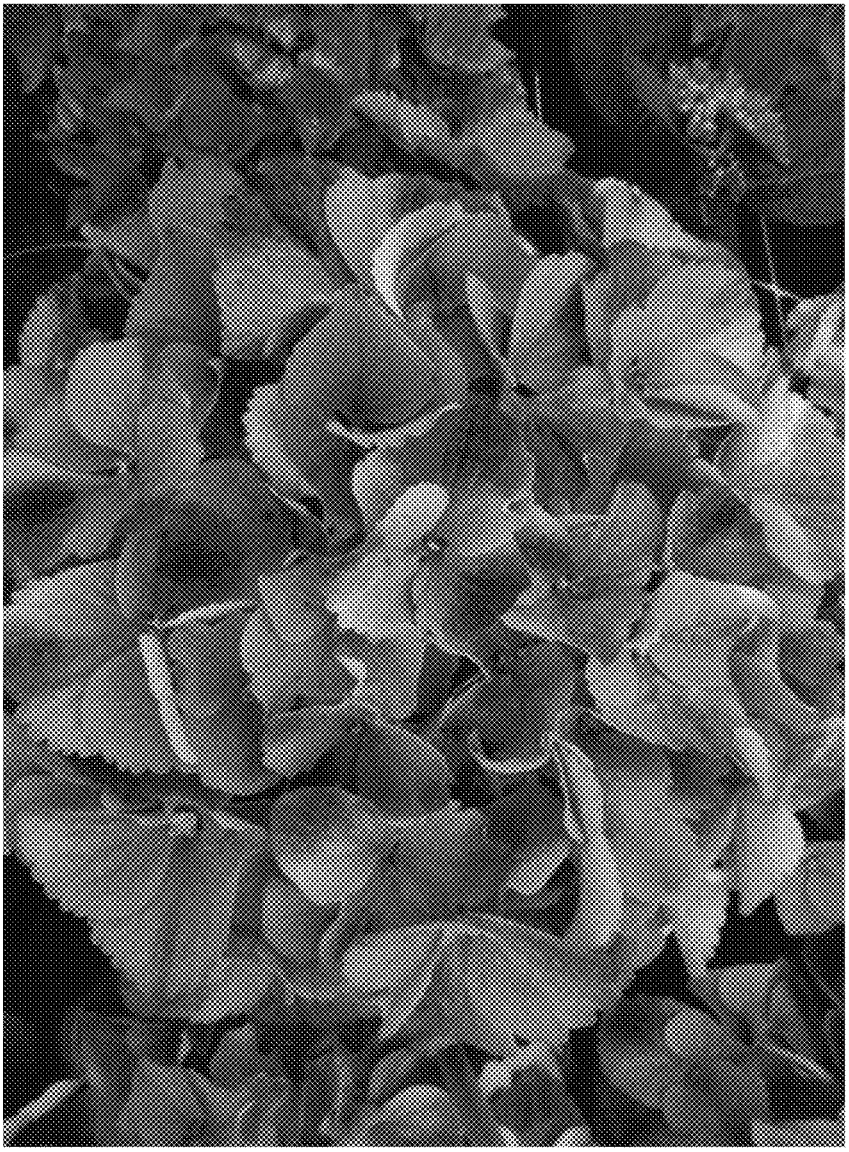

The photograph in FIG. 4 provides a view of an inflorescence when plants were grown with aluminum sulfate and a soil pH of <6.5.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Hokomalega' as grown in a greenhouse in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Late spring to late summer with flowers showy at least for 2 months in the Netherlands.

*Plant type*.—Deciduous shrub, mophead type *Hydrangea*.

*Plant habit*.—Broad spreading, upright.

*Height and spread*.—An average of 56.6 cm in in height and 70 cm in spread as grown in a 13-cm container, reaches 1 m in height and spread as a 3-year-old plant in the landscape.

*Hardiness*.—At least in U.S.D.A. Zones 5 to 9.

*Diseases and pests*.—No susceptibility and resistance to diseases or pests has been observed.

*Root description*.—Fine and fibrous, 161C in color.

*Propagation*.—Stem cuttings.

*Root development*.—An average of 6 weeks for root initiation with a young rooted plant produced in an average of 18 weeks.

*Growth rate and vigor*.—Moderate.

Stem description:

*Stem shape*.—Rounded.

*Stem strength*.—Strong.

*Stem color*.—Young; 144A, mature; 144B, internodes slightly tinged with N186C, old bark; 199B to 199C.

*Stem size*.—An average of 35.4 cm in length (excluding inflorescence) and 8.9 mm in diameter.

*Stem surface*.—Glabrous and sparsely covered with lenticels that are an average of 3 mm in length and 1 mm in diameter, N186C in color.

*Stem aspect*.—Average angle of vertical to 25°, varying between 0° and 50°.

*Internode length*.—An average of 8.9 cm.

*Branching*.—Freely branching with an average of 17 lateral branches.

Foliage description:

*Leaf shape*.—Broad ovate to broad elliptic.

*Leaf arrangement*.—Opposite.

*Leaf division*.—Simple.

*Leaf base*.—Short attenuate.

*Leaf apex*.—Short apiculate.

*Leaf margins*.—Coarsely serrate.

*Leaf venation*.—Pinnate, color; color upper surface 146C, lower surface 146D.

*Leaf size*.—An average of 12.1 cm in length and 8.9 cm in width.

*Leaf attachment*.—Petiolate.

*Leaf number*.—An average of 8 to 10 per lateral stem.

*Leaf surface*.—Both surfaces; smooth and slightly glossy.

*Leaf color*.—Young foliage; upper surface 144A, lower surface 144B, mature foliage; upper surface 137A, lower surface 148B.

*Petioles*.—An average of 1.9 cm in length and 4 mm in diameter, upper and lower surface color 144B, both surfaces are smooth and slightly glossy.

Inflorescence description:

*Inflorescence type*.—Terminal panicle, flattened mophead comprised of a sterile flowers above fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 9.6 cm in height and 15.1 cm in diameter.

*Flower number*.—An average of 100 sterile flowers and 25 fertile flowers per panicle.

*Flower fragrance*.—None.

*Flower aspect*.—Sterile flowers; upright to outward, fertile flowers; upright.

*Flower size*.—Sterile flowers; an average of 4 cm in diameter and 2 cm in depth, fertile flowers; an average of 1 cm in diameter and 9 mm in depth.

*Flower type*.—Rotate.

*Flower buds*.—Sterile flowers; an average of 1 cm in length and 2 cm in diameter, broadly cup shaped, 145C, tips of immature sepals strongly tinged 50C in color, fertile flowers; an average of 5 mm in length and 4 mm in diameter, obovate in shape, color; 51D, changing to 51C at the top, immature sepals 145C with tips 144A and immature ovary 145C.

*Peduncles*.—Strong, flattened oval in shape, an average of 2 cm in length and 2 mm in width on primary peduncles and secondary peduncles 1 cm in length and 1.8 mm in width, 183A and 185A in color, surface matte and moderately covered with thin pubescence an average of 0.2 mm in length and too small to measure color.

*Pedicels*.—Sterile flowers; held primarily at an average angle of 30°, an average of 2.3 cm in length and 1.25 mm in diameter, moderately strong strength, 59D in color, surface matte and moderately covered with thin pubescence an average of 0.2 mm in length and too small to measure color, fertile flowers; held at an average angle of 25° from vertical, an average of 5 mm in length and 1 mm in diameter, moderate strength, 62B in color, matte surface and moderately covered with thin pubescent hairs an average of 0.2 mm in length and too small to measure color.

*Petals*.—Sterile flowers; an average of 4, rotate, cruciform in arrangement, acute apex, cuneate base, entire margins, ovate to moderately concave in shape, average of 4 mm in length and 2 mm in width, both surfaces; smooth, glabrous and matte, color; when opening and fully open upper surface 68B, changing to N155B at the base and margins, when opening and fully open lower surface 65C, changing to N155B at the base and margins, fertile flowers; an average 5, rotate in arrangement, ovate and concave in shape, entire margin, acute apex, cuneate base, an average of 4.5 mm in length and 2.5 mm in width, upper and lower surface glabrous and matte, color; upper surface when opening and fully open 68B, changing to N155B at the top, base and margins, lower surface when opening and fully open 65C, changing to N155B at the base.

*Sepals*.—Sterile flowers; 4, rotate, broadly and bluntly acute apex with an emarginate outer tip, broadly cuneate base, entire to slightly undulate margins occasionally 1 or 2 small teeth near the top, reniform to nearly deltoid in shape, an average of 2 cm in length and 2.4 cm in width, upper and lower surface glabrous and matte, color; when opening upper 63C, when opening lower surface 62C, when fully open upper surface N57C, when fully open lower surface 63C, upper surface fading to 146D, tinged 179D at the base, veined 58C, lower surface fading to 195B, veined 58C, surface fertile flowers; an average of 5, deltoid in shape, entire margin, broadly acute apex, 1 mm in length, 2 mm width, and broadly cuneate base, both surfaces are glabrous and matte, color; upper surface when opening and fully open 145C, lower surface when opening 145C, tip 144A, lower surface when fully open 145C, tip 144B.

*pH sensitivity*.—The inflorescence color will experience a blueing effect when grown with added aluminum sulfate and a soil pH of less that 6.5, plants have not been grown under these conditions except for trial purposes, sepals of the sterile flowers at maturity on both surfaces is a blend of N80C, 75A, and 138A, the bueing coloration of the fertile flowers has not been recorded.

Reproductive organs:

*Gynoecium*.—Sterile flowers; 2 to 3 pistils, an average of 1 mm in length, stigma; club-shaped and NN155D in color, style; 0.5 mm in length, NN155A in color, ovary is NN155A in color, fertile flowers; an average of 2 to 3 pistils, an average of 1 mm in length, stigma; club-shaped and NN155C in color, style; 0.5 mm in length and NN155D in color, ovary is 145C in color.

*Androecium*.—Sterile flowers; an average of 8 stamens, filaments; an average of 2.25 mm in length and NN155D in color, anthers; broad oblong in shape, an average of 0.75 mm in length and 155D in color, pollen; moderate in quantity, 155A in color, fertile flowers; an average of 10 stamens, filaments; an average of 5 mm in length and NN155D in color, anthers; broad oblong in shape, an average of 0.75 mm in length and 155D in color, pollen; moderate in quantity and 155A in color.

*Fruit and seed*.—None observed.

It is claimed:

1. A new and distinct cultivar of *Hydrangea* plant named 'Hokomalega' substantially as herein illustrated and described.

* * * * *